United States Patent
Dufresne et al.

(12) 
(10) Patent No.: US 6,589,479 B2
(45) Date of Patent: Jul. 8, 2003

(54) METHOD OF MONITORING STERILIZATION AND INDICATOR THEREFOR

(75) Inventors: Sylvie Dufresne, Charlesbourg (CA); Robert Boulay, Laval (CA)

(73) Assignee: Technologies of Sterilization with Ozone TSO3, Inc. (CA)

( * ) Notice: Subject to any disclaimer, the term of this patent is extended or adjusted under 35 U.S.C. 154(b) by 0 days.

(21) Appl. No.: 09/880,443

(22) Filed: Jun. 13, 2001

(65) Prior Publication Data

US 2002/0012610 A1 Jan. 31, 2002

(30) Foreign Application Priority Data

Jun. 14, 2000 (CA) ............................................. 2311509

(51) Int. Cl.[7] .................................................. A61C 9/00
(52) U.S. Cl. ............................. 422/28; 422/29; 435/31; 436/166
(58) Field of Search ........................ 422/28, 29; 436/1, 436/166; 424/333; 435/31

(56) References Cited

U.S. PATENT DOCUMENTS

| | | | |
|---|---|---|---|
| 3,704,096 A | | 11/1972 | Verses et al. |
| 5,518,927 A | | 5/1996 | Malchesky et al. |
| 5,855,856 A | * | 1/1999 | Karlson ................. 422/186.11 |
| 5,942,438 A | * | 8/1999 | Antonoplos et al. ........... 436/1 |
| 6,410,338 B1 | * | 6/2002 | Lippold et al. ................ 422/29 |

FOREIGN PATENT DOCUMENTS

| | | | |
|---|---|---|---|
| EP | 0 914 833 | | 5/1999 |
| EP | 0 052 507 | | 11/2000 |
| GB | 2219084 A | * | 11/1989 |
| JP | 002230517 | | 5/1996 |
| JP | 11083834 A | * | 3/1999 |
| WO | WO 98/46994 | | 10/1998 |
| WO | WO 98/58683 | | 12/1998 |
| WO | WO 00/61200 | | 10/2000 |

OTHER PUBLICATIONS

Vol. 1.3 Sterilization Part 3 Industrial Process Control of the Association for the Advancement of Medical Instrumentation (AAMI) Standard Recommended Practice and American Standard Institute (ANSI), 1996.

* cited by examiner

Primary Examiner—Robert J. Warden, Sr.
Assistant Examiner—Sean E. Conley
(74) Attorney, Agent, or Firm—Pendorf & Cutliff

(57) ABSTRACT

The invention relates to a method of monitoring a sterilization process having an oxidation-type sterilant, said process comprising the steps of: providing an indicator compound capable of exhibiting a color change upon exposure to the sterilant, the indicator compound being free of heterocyclic nitrogen, diazo nitrogen and amino nitrogen, and selected from the group consisting of anthraquinone dyes, triarylmethane dyes and xanthene dyes; exposing the indicator compound to the sterilization process; and observing the compound for a change of colour. The invention also relates to an indicator for an ozone sterilization process. A preferred indicator compound is rosolic acid.

4 Claims, No Drawings

METHOD OF MONITORING STERILIZATION AND INDICATOR THEREFOR

FIELD OF THE INVENTION

The invention relates to a method of monitoring the progress of an oxidation-type sterilization process and a chemical indicator therefor, in particular an ozone sterilization process.

BACKGROUND OF THE INVENTION

Sterilization is important in many fields, especially in medicine. One means of sterilization uses ozone gas as a sterilizing agent. One such method for sterilizing medical instruments uses a sealed device such as the TSO3-125L (available from TSO3). The effectiveness of ozone increases with increased humidity and therefore, with humidified ozone, sterilization can be effected at low temperatures, even at room temperature. This reduces the need for high temperature apparatus and permits use of less ozone. Using lower temperatures is also an advantage since ozone is temperature sensitive and decomposes rapidly at higher temperatures.

Naturally, it is important to be able to monitor a sterilization procedure to verify that sterilization has been effective.

Conventionally, sterilization can be verified by placing indicators in the sterilization chamber with the medical instruments load. Chemical and biological indicators are both used to monitor sterilization. A chemical indicator is designed to provide a characteristic color change in response to one or more of the physical conditions within the sterilizing chamber. Chemical indicators are often integrated with other sterilization verification devices to provide additional evidence of exposure to sterilant. Biological indicators are composed of strips containing a high number of micro-organisms. After sterilization is complete, the strip is cultured to see if all the micro-organisms have been killed. If the sterilization is successful, no growth will be observed. Such procedures are generally required by local health and safety regulations.

If this were the only means of verifying adequate sterilization, the articles sterilized could not be used for at least 24 hours. This imposes inconvenient storage or inventory requirements which may not be possible, for example, in some hospitals. Therefore there is a need for a means to monitor the sterilization more quickly.

Chemical indicator performance is explained in more detail in Volume 1.3 Sterilization Part 3 Industrial Process Control of the Association for the Advancement of Medical Instrumentation (AAMI) Standard Recommended Practice and American Standard Institute (ANSI).

U.S. Pat. No. 5,518,927 (Malchesky et al) discloses an indicator compound. However, the compounds disclosed are unstable and change colour over time, especially when exposed to light, and therefore they are not reliable. Further, they are not suitable, for some oxidation-type sterilants. For example, for ozone, they change colour even when the ozone is dry and non-sterilizing. Also, dyes taught in this reference, are carcinogenic.

It is an object of the present invention to provide a means to monitor sterilization in an oxidation-type sterilization process, particularly an ozone sterilization process.

SUMMARY OF THE INVENTION

According to the present invention there is provided a method of monitoring a sterilization process having an oxidation-type sterilant, said process comprising the steps of:

providing an indicator compound capable of exhibiting a colour change upon exposure to the sterilant, the indicator compound being free of heterocyclic nitrogen, diazo nitrogen and amino nitrogen, and selected from the group consisting of anthraquinone dyes, triarylmethane dyes and xanthene dyes;

exposing the indicator compound to the sterilization process; and observing the compound for a change of colour.

According to another aspect of the present invention there is provided an indicator for an ozone sterilization process comprising an ozone indicator compound and a substrate.

According to another aspect of the present invention there is provided a use of an ozone indicator compound in the manufacture of an indicator for a sterilization process having humidified ozone as the sterilant.

DETAILED DESCRIPTION OF THE INVENTION

Oxidation-type sterilization includes the use of sterilants such as ozone, peroxide, chlorine dioxide and peracetic acid. In the present invention, the preferred sterilant is ozone.

It has now been found that certain compounds are suitable for monitoring oxidation-type sterilization processes such as those which use humidified ozone as a sterilant. A suitable compound is a compound which exhibits a visible change or a colour change upon exposure to the sterilization process. A colour change includes: a change of one colour to another colour; a change from a darker colour to a lighter colour; a change from a light colour to a darker colour; or a change from one colour to the absence of colour such as bleaching.

In choosing an appropriate indicator compound there are various criteria to be considered. Since a sterilization process is often followed by medical use of the sterilized items, it is preferable that the indicator compound is non-toxic and does not produce toxic compounds under the conditions of the process. For this reason, certain nitrogen containing compounds such as azo dyes may be unsuitable.

It is preferable that the indicator compound is light stable, especially to fluorescent light or sunlight, so that the colour of the compound is not affected even after lengthy exposure to light such as might be encountered during storage in a clinic or hospital in a lighted room.

Preferably either the initial colour is dark and the changed colour after sterilization is light or is clearly contrasting to the initial colour, or the initial colour is light or colourless and the changed colour, after sterilization, is dark or darker. A colour change from one colour to a different colour, or from one colour to colourless (such as bleaching) is also preferred.

In some sterilization procedures, the sterilization is repeated. Thus the sterilization proceeds in two half cycles. In the first half cycle the item to be sterilized is exposed to humidified ozone, for example, and then the ozone is removed. This half cycle is then followed by another half cycle i.e. another exposure to humidified ozone. In such a two-step process, a preferred indicator compound would show two separate colour changes corresponding to each of the two half cycles. In this way it is possible to verify successful completion of each cycle.

Since the purpose of the indicator compound is to monitor actual sterilization, there should be no colour changes (or a colour change which is different from the sterilization colour change) when no sterilization has occurred. Thus in an ozone sterilization, in dry ozone (which is far less effective for sterilization than humidified ozone) there should be no colour change. Further, the colour of the compound should be stable to air to prevent handling complications and preferably stable to oxygen, since some sterilization procedures use oxygen as a flushing medium to flush the sterilant, such as ozone, from the sterilization chamber or as a carrier for the sterilant.

Since it is preferred that the indicator compound does not form toxic products, the present invention is preferably directed to indicator compounds free of nitrogen particularly those free of reduced nitrogen. Thus the diazo groups (of azo dyes), heterocyclic nitrogen atoms and amino nitrogen groups are preferably avoided. Such forms of nitrogen are usually oxidizable to toxic nitrogen compounds. However, usually groups with nitrogen in oxidized form such as —$NO_3$ and —$NO_2$ would be suitable for use. Also, it is preferred to avoid sulphur or sulphur groups in which the sulphur is oxidizable to avoid formation of toxic sulphur compounds such as $SO_3$ and $SO_2$. However, usually groups with sulphur in an oxidized form such as —$SO_3H$ and —$SO_4$ would be suitable for use. Halogen substituents are usually acceptable although they may interfere with an ozone process by reacting with the ozone (and therefore using up ozone which would otherwise be available for sterilization). Suitable indicator compounds are selected from anthraquinone dyes, triarylmethane dyes and xanthene dyes.

Anthraquinone dyes are structurally derived from anthraquinone. They may be hydroxyl substituted and include such compounds as alizarin and alizarin red.

Triarylmethane dyes, also known as triphenylmethane dyes include compounds belonging to the generic class of compounds of formula I:

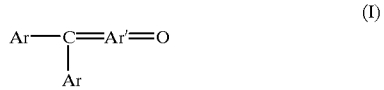

(I)

in which Ar is substituted or unsubstituted aryl and Ar' is a substituted or unsubstituted cyclohexadiene group. Preferably Ar is phenyl or substituted phenyl. Suitable substituents include hydroxyl, halo, such as bromo or chloro, lower alkyl, such as methyl, ethyl or isopropyl, sulphonate and carboxyl. Preferably at least one of the Ar groups has a hydroxyl group. This class of compounds includes phenol red. A particularly preferred compound is rosolic acid, especially for an ozone sterilization.

Xanthene dyes include compounds belonging to the class of compounds derived from the structure of formula II:

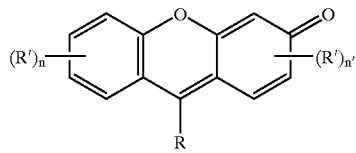

(II)

in which each R' may be independently a substituent such as hydroxyl, halo (for example bromo, chloro or iodo), sulphonate, lower alkyl (such as methyl, ethyl or propyl), lower alkoxy (such as methoxy), lower alkoxy carbonyl (such as methoxycarbonyl or ethoxycarbonyl) or carbonyl, n is an integer of 1 to 4 and n' is an integer of 1 to 3. R may be aryl such as unsubstituted or substituted phenyl (suitable substituents including those listed for R' above) or non-aryl such as alkyl (such as methyl, ethyl, or propyl), haloalkyl (such as trichloromethyl) or cycloalkyl (such as cyclohexyl). Preferably R is aromatic and at least one R' is hydroxyl. Xanthene dyes include such compounds as gallein.

Rosolic acid (available from J. T. Baker) is also known as Aurin, Corallin yellow and Corallin free acid (CAS number 603-45-2) and has the formula

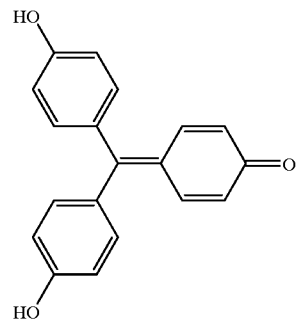

This compound not only changes colour during an ozone sterilization, it can exhibit a double visual change in a two half cycle sterilization process. This compound is red in the initial state, changes to a yellow-orange or light orange colour after the first half cycle, and then, at the end of the second half cycle, or at the completion of sterilization, it becomes markedly paler in colour or colourless.

In use, the indicator compound is placed in the same sterilizing conditions as an article to be sterilized, to monitor the effectiveness of the sterilization by a change in colour. Usually an indicator compound is placed adjacent a particular item, or even attached to it or placed inside it. A separate portion of indicator compound is usually used for each item to be sterilized. For convenience, the indicator compound is preferably formulated as an ink composition. Such a composition can then be used to coat or impregnate a substrate. A suitable substrate is paper. The coated or impregnated paper may be in the form of a narrow roll so that convenient short strips may be readily torn or detached from the roll to use in the sterilization. The coated or impregnated paper may be protected from handling by a transparent film, or strips of the paper may be inserted into pouches, such as Tyvek pouches, which allow exposure of the strip to the sterilant while permitting observation of any colour change through a transparent film.

The indicator comprises a material having a section of indicator compound thereon. The indicator compound, as described, may be incorporated with a number of different devices, such as a stand alone chemical strip, a self-contained biological indicator incorporating an indicator compound, a challenge pack, a test pack, tape or stickers, pouches, a limited re-use monitor, a warranty indicator, a tamper-evident device, and a documentation record (instrument count sheet).

In a preferred embodiment, an indicator is formed by placing the indicator compound on a strip of material to form an indicator strip. Indicator strips comprise generally small pieces of material having an indicator compound section thereon. The indicator strip is placed in a sterilization chamber and thereby exposed to an oxidation-type sterilant. Upon exposure for sufficient time to the sterilant, the indicator portion of the strip changes colour.

Indicator strips are made in a way which is standard for applying dye to a strip of material. The indicator compound may be sprayed, pressed, silk-screened, embedded, or brushed onto the strip. One of ordinary skill in the art is aware of the method of applying dye to a material, such as paper, plastic or a metallic surface so the process is not described in detail herein. The indicators may be placed in a sterilization chamber alone or as part of a test pack or challenge pack, described below.

The indicator compound may also be integrated with a self-contained biological indicator. It is further contemplated that the indicator compound could be used to display a colour key thereby providing visual colour comparison to determine when the indicator compound has sufficiently changed colour and which colour indicates an unsterilized state and which colour indicates a sterilized state.

It is also contemplated that the indicator compound may be incorporated with fabric of the type worn by a medical professional or of the type described above for use with a chemical indicator tape that will be exposed to a sterilization process using an oxidant. The dye would be impregnated into the fabric to indicate full exposure to a sterilant.

As mentioned above, the indicator compound may be incorporated into an ink composition. The preparation of suitable ink compositions is known to those skilled in the art. Besides the dye or indicator compound, an ink composition might include: a solvent; a pH adjuster; a binder; a viscosity modifier; a defoamer; an oil base or carrier; and evaporation or drying aids. A suitable solvent might be water or alcohol. Binders include water soluble acrylic resins. Viscosity modifiers include hydroxyethyl cellulose. Defoamers include non-ionic mineral oils. pH adjusters include alkalis such as sodium hydroxide and ammonia. Oil bases or carriers include non-foaming non-ionic mineral oils. Evaporation or drying agents include compounds which are also suitable for the other functions such as ammonia and alcohol.

EXAMPLES

A number of compounds were tested for suitability as indicator compounds to monitor an ozone sterilization process. The compounds were assessed in three areas: colour acceptability; colour changes; and colour stability.

Acceptability refers to the acceptability of the initial colour state. For some compounds, the initial colour was considered to be not dark enough, or too pale, such as carminic acid, gallein, carmine and aurintricarboxylic acid. The results are shown below in Table 1.

Those compounds considered to have an acceptable dark colour were then tested for colour changes. For a colour indicator in an ozone sterilization process, the compound should preferably exhibit a clear colour change.

Also, it is preferable that the compound show a different colour change or no colour change when the sterilizing ozone is dry, since effective ozone sterilization is enhanced by increased humidity.

Further, it is preferred that the compound give a different colour change or no colour change in contact with oxygen. Otherwise, it might not be possible to distinguish the effectiveness of the sterilization from an oxygen flushing step, since some sterilization procedures use an oxygen flushing step to flush out the sterilant after sterilization.

In a preferred sterilization procedure, using ozone, the ozone sterilization is repeated as two sterilization cycles. In this procedure, it would be further preferred to have a compound which exhibited an additional, or further distinct colour change so that the effectiveness of each cycle could be monitored.

To test for the above situations, sample test strips were prepared as follows. Portions of each compound to be tested were dissolved in 25 ml of distilled water or methanol. Where necessary, the pH was adjusted with 0.1 N sodium hydroxide solution to obtain the correct initial colour. Further distilled water was added to make up the volume to 100 ml. Unless otherwise stated, the compounds were used in the form of a 0.1% solution. Paper strips were then soaked in the solutions and allowed to dry at room temperature to obtain the test strips. The initial colour was noted. The results are shown below in Table 1.

TABLE 1

Initial Colour Acceptability

| Compound name | Colour | Acceptability |
|---|---|---|
| Carminic acid | pale pink | not dark enough |
| Gallein | mauve or dark red | not dark enough |
| Carmine | mauve | not dark enough |
| Carminic acid (1%) | mauve | not dark enough |
| Aurintricarboxylic acid | brown | not dark enough |
| Alizarin red | mauve | acceptable |
| Alizarin | mauve | acceptable |
| Sirius red | red | acceptable |
| Phenol red | red | acceptable |
| Safranine O | pink | acceptable |
| Rosolic acid | red | acceptable |

The above compounds are commercially available as follows: Gallein, Carminic acid, aurintricarboxylic acid, Rosolic Acid, Alizarin red and Alizarin (all available from J. T. Baker); and Sirius red and Teflon red (available from Bayer Aktiengesellschaft).

A test strip for each compound was then exposed to a sterilizing quantity of humidified ozone in a 125L sealed sterilization chamber, and then exposed to a further sterilizing quantity of ozone in a second cycle. Exposure to the ozone lasted between 30 minutes and 1 hour for each half cycle. When testing for the first half cycle the strips were removed and kept as a record. When testing for the complete cycle (both first and second half cycles), fresh strips were used at the beginning of the first half cycle and were not removed until the end of the second half cycle. In this latter test, the humidified ozone for the first half cycle was removed by vacuum and a fresh sterilizing quantity of humidified ozone was introduced into the chamber. If necessary, to obtain a darker colour for easier identification at the end of the first half cycle, a more concentrated solution was used to prepare the strips, such as a 2, 3 or 5 g/L solution. Additional test strips were then exposed to a comparative quantity of dry ozone in the same sterilization chamber. Finally test strips were exposed to oxygen (in the absence of ozone) in the same sterilization chamber. The results are shown below in Table 2.

TABLE 2

Colour Changes

| Compound name | before exposure | after half-cycle | after complete cycle | ozone without humidity | Humidity with oxygen |
|---|---|---|---|---|---|
| Rosolic Acid mixed with printing base 8% (2 layers) | red | light orange | colourless | dark-orange | no change |
| Rosolic Acid 1% | red | yellow-orange | colourless | red-pink | red-pink |

TABLE 2-continued

Colour Changes

| Compound name | before exposure | after half-cycle | after complete cycle | ozone without humidity | Humidity with oxygen |
|---|---|---|---|---|---|
| Phenol red | red-orange | colourless | colourless | yellow-orange | yellow-orange |
| Safranin O | dark pink | pink | colourless | pink | pink |
| Sirius red | pink-red | peach | yellowish | no change | pink |
| Sterrad* | pink | colourless | colourless | yellow | yellow |
| Kimberly-Clark** | blue | mauve | mauve | mauve | no change |

*Commercially available Indicator strip REF 14100 from STERRAD ™ (made by ASP, a division of Johnson & Johnson)
**Commercially available gas plasma indicator strip 66004 from Kimberly-Clark One of the samples tested in Table 2 was an 8% Rosolic acid ink composition prepared by mixing rosolic acid with a printing base. The composition was as follows:

| component | percentage by weight |
|---|---|
| water | 84.9 |
| rosolic acid | 8.0 |
| hydroxyethyl cellulose | 3.15 |
| sodium hydroxide | 1.8 |
| acrylic resin | 1.5 |
| ammonia | 0.45 |
| non-foaming non-ionic mineral oil | 0.2 |

This composition was then applied to paper strips and allowed to dry. A second layer, to intensify the colour, was then applied. These two-layer strips were then tested as above.

Three of the compounds which seemed most promising from the results in Table 2 were selected for the last group of tests, for colour stability. The test strips were exposed to an autoclave and to light (one group of strips for 21 days in fluorescent light and a second group of strips for 21 days near a window for exposure to sunlight). The results of these tests are shown in Table 3. One of the samples tested was the rosolic acid ink composition described above for Table 2.

TABLE 3

Colour Stability

| Compound name | autoclave | light |
|---|---|---|
| Rosolic Acid mixed with printing base 8% (2 layers) | no change of colour | no change of colour |
| Rosolic acid 1% | no change of colour | no change of colour |
| Phenol red | no change of colour | fading when exposed to light |
| Safranin O | no change of colour | fading when exposed to light |

What is claimed is:

1. A method of monitoring a sterilization process having humidified ozone as sterilant, said process comprising the steps of:

a) providing an indicator compound capable of exhibiting a colour change upon exposure to the humidified ozone, but does not exhibit a colour change upon exposure to dry ozone or oxygen, the indicator compound being free of heterocyclic nitrogen, diazo nitrogen and amino nitrogen, and selected from the group consisting of anthraquinone dyes, triarylmethane dyes and xanthene dyes;

b) exposing the indicator compound to the sterilization process; and c) observing the compound for a change of colour.

2. A method according to claim 1 wherein the indicator compound is light stable.

3. A method according to claim 1, wherein the indicator compound is a compound of the formula I

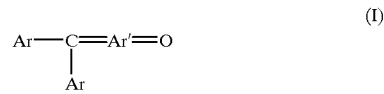

in which Ar is aryl and Ar' is a cyclohexadiene group.

4. A method according to claim 1 wherein the indicator compound is rosolic acid.

* * * * *